(12) United States Patent
Hernandez et al.

(10) Patent No.: US 11,969,605 B2
(45) Date of Patent: Apr. 30, 2024

(54) SYSTEMS AND METHODS FOR NOISE FILTERING IN IMPLANTABLE MEDICAL DEVICE CHARGING SYSTEMS

(71) Applicant: Advanced Neuromodulation Systems, Inc., Plano, TX (US)

(72) Inventors: Luis Ortiz Hernandez, Plano, TX (US); Santhosh Seetharaman, Plano, TX (US); Seil Oh, Dallas, TX (US); Edward Lundberg, Frisco, TX (US); Nicholas Sachs, Los Angeles, CA (US); Hongxuan Zhang, Austin, TX (US); William Winstrom, Leander, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 435 days.

(21) Appl. No.: 17/412,802

(22) Filed: Aug. 26, 2021

(65) Prior Publication Data

US 2022/0193426 A1 Jun. 23, 2022

Related U.S. Application Data

(60) Provisional application No. 63/129,882, filed on Dec. 23, 2020.

(51) Int. Cl.
*A61N 1/372* (2006.01)
*A61N 1/378* (2006.01)

(52) U.S. Cl.
CPC ....... *A61N 1/3787* (2013.01); *A61N 1/37223* (2013.01); *A61N 1/37247* (2013.01)

(58) Field of Classification Search
CPC .............. A61N 1/3787; A61N 1/37223; A61N 1/37247
See application file for complete search history.

(56) References Cited

U.S. PATENT DOCUMENTS

| | | | |
|---|---|---|---|
| 7,813,801 B2 | 10/2010 | Youker et al. | |
| 8,214,042 B2 | 7/2012 | Ozawa et al. | |
| 8,989,869 B2 * | 3/2015 | Torgerson | A61N 1/36142 607/61 |

(Continued)

OTHER PUBLICATIONS

International Search Report and Written Opinion, PCT/US2021/064572, dated Mar. 31, 2022, 14 pages.

*Primary Examiner* — Eugene T Wu
(74) *Attorney, Agent, or Firm* — Armstrong Teasdale LLP

(57) ABSTRACT

The present disclosure provides systems and methods for wirelessly charging an implantable medical device. An external charging device includes a coil, signal generating circuitry to drive current through the coil at a charging frequency to induce current in a second coil in the implantable medical device, monitoring circuitry to generate an output signal to monitor charging operations, and a comb filter. The comb filter is configured to apply filtering to the output signal to remove noise from the output signal, wherein the filtering is applied based on the charging frequency. The external charging device is configured to process the filtered output signal to detect a circuit state of charging circuitry of the implantable medical device during charging operations, and the external charging device is configured to vary the charging frequency based, in part, on detection of the circuit state of the charging circuitry of the implantable medical device.

20 Claims, 6 Drawing Sheets

(56) References Cited

U.S. PATENT DOCUMENTS

| | | | |
|---|---|---|---|
| 9,225,190 | B2 | 12/2015 | Labbe et al. |
| 9,887,574 | B2 | 2/2018 | Angara et al. |
| 9,998,238 | B2 | 6/2018 | Saada et al. |
| 10,938,255 | B2 * | 3/2021 | Smith .................. H03K 17/955 |
| 2008/0132974 | A1 | 6/2008 | Strother et al. |
| 2010/0138176 | A1 * | 6/2010 | Yu ...................... G01R 31/3828 |
| | | | 702/63 |
| 2013/0184785 | A1 | 7/2013 | Aghassian |
| 2016/0248280 | A1 | 8/2016 | Ben-Shalom et al. |
| 2021/0074421 | A1 | 3/2021 | Gopalakrishnan |

* cited by examiner

SYSTEMS AND METHODS FOR NOISE FILTERING IN IMPLANTABLE MEDICAL DEVICE CHARGING SYSTEMS

CROSS-REFERENCE TO RELATED APPLICATIONS

This application claims priority to provisional application Ser. No. 63/129,882, filed Dec. 23, 2020, which is incorporated herein by reference in its entirety.

A. FIELD OF THE DISCLOSURE

The present disclosure relates generally to charging implantable medical devices, and more particularly to filtering out noise from signals generated by an external charging device.

B. BACKGROUND ART

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. Other examples include deep brain stimulation, cortical stimulation, cochlear nerve stimulation, peripheral nerve stimulation, vagal nerve stimulation, sacral nerve stimulation, etc.

In addition to neurostimulation (NS) systems, several other medical devices exist today, including but not limited to electrocardiographs (ECGs), electroencephalographs (EEGs), squid magnetometers, implantable pacemakers, implantable cardioverter-defibrillators (ICDs), electrophysiology (EP) mapping and radio frequency (RF) ablation systems, and the like, that may be implanted within a patient for facilitating therapy and/or diagnostics.

In general, implantable medical devices or IMDs are configured to be implanted within a patient anatomy and commonly employ one or more leads with electrodes that either receive or deliver voltage, current, or other electromagnetic pulses from or to an organ or tissue for diagnostic or therapeutic purposes In order to provide consistent therapy and reliable operation over a substantial duration of time, IMDs are often provided with one or more batteries that may be charged and recharged to store energy, which may supply power to the rest of the IMD circuitry and associated lead systems.

Because IMDs are implanted within patients, the IMDs are typically charged by an external charger that transmits energy wirelessly into the IMDs, such as through radio frequency (RF) signals. It is desirable that an IMD is generally charged as quickly and safely as possible within certain ranges depending upon the therapy application. It is further desired that wireless energy transfer between the external charger and the IMD's charging circuitry be performed as efficiently as possible.

BRIEF SUMMARY OF THE DISCLOSURE

In one embodiment, the present disclosure is directed to an external charging device for wirelessly charging an implantable medical device. The external charging device includes a coil, signal generating circuitry coupled to the coil to drive current through the coil at a charging frequency to induce current in a second coil in the implantable medical device, monitoring circuitry coupled to the coil to generate an output signal to monitor charging operations, and a comb filter coupled to the monitoring circuitry. The comb filter is configured to apply filtering to the output signal generated by the monitoring circuitry to remove noise from the output signal, wherein the filtering is applied based on the charging frequency. The external charging device is configured to process the filtered output signal to detect a circuit state of charging circuitry of the implantable medical device during charging operations, and the external charging device is configured to vary the charging frequency based, in part, on detection of the circuit state of the charging circuitry of the implantable medical device.

In another embodiment, the present disclosure is directed to a wireless charging system including an implantable medical device including charging circuitry and an external charging device configured to wirelessly charge the implantable medical device. The external charging device includes a coil, signal generating circuitry coupled to the coil to drive current through the coil at a charging frequency to induce current in a second coil in the implantable medical device, monitoring circuitry coupled to the coil to generate an output signal to monitor charging operations, and a comb filter coupled to the monitoring circuitry. The comb filter is configured to apply filtering to the output signal generated by the monitoring circuitry to remove noise from the output signal, wherein the filtering is applied based on the charging frequency. The external charging device is configured to process the filtered output signal to detect a circuit state of charging circuitry of the implantable medical device during charging operations, and the external charging device is configured to vary the charging frequency based, in part, on detection of the circuit state of the charging circuitry of the implantable medical device.

In yet another embodiment, the present disclosure is directed to a method for operating an external charging device in a wireless charging system. The method includes driving, using signal generating circuitry of the external charging device, current through a coil at a charging frequency to induce current in a second coil in an implantable medical device, generating, at monitoring circuitry of the external charging device, an output signal to monitor charging operations, and applying, using a comb filter of the external charging device, filtering to the output signal generated by the monitoring circuitry to remove noise from the output signal, the filtering applied based on the charging frequency. The method further includes processing the filtered output signal to detect a circuit state of charging circuitry of the implantable medical device during charging operations, and varying the charging frequency based, in part, on detection of the circuit state of the charging circuitry of the implantable medical device.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
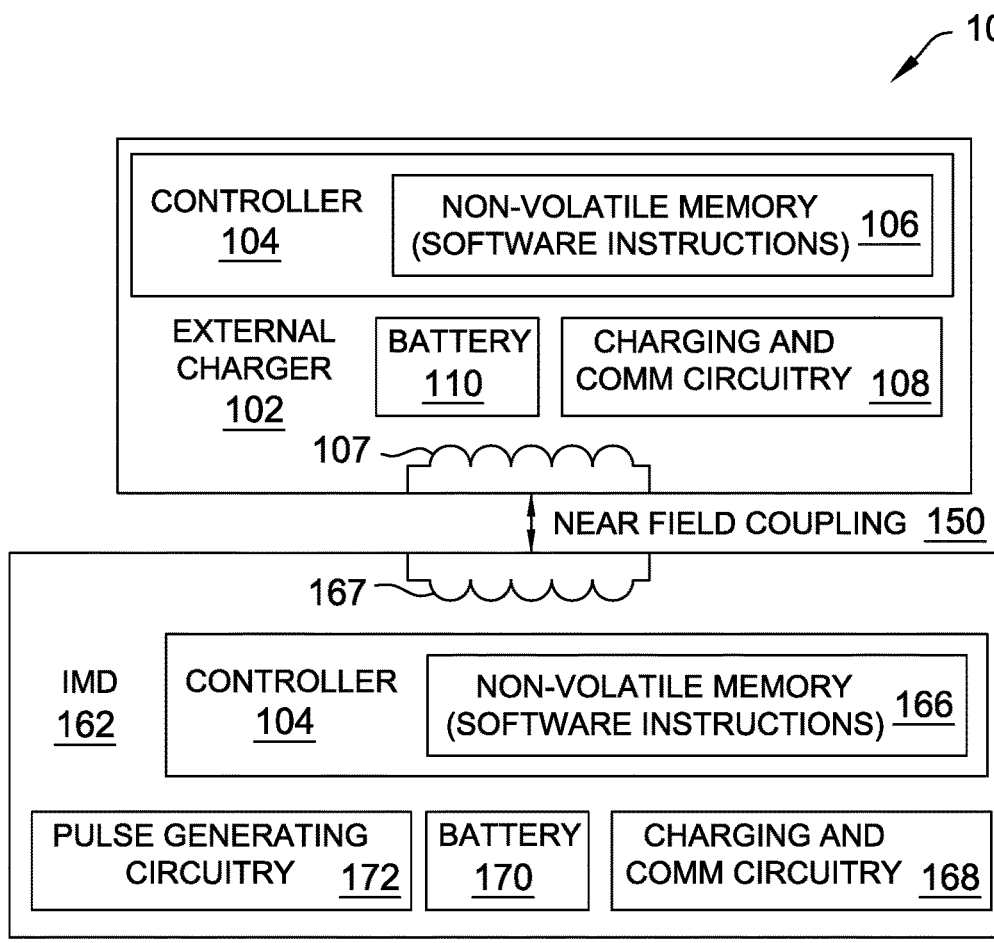
FIG. 1 is a block diagram of one embodiment of a charging system.

The present disclosure provides systems and methods for wirelessly charging an implantable medical device. An external charging device includes a coil, signal generating circuitry to drive current through the coil at a charging frequency to induce current in a second coil in the implantable medical device, monitoring circuitry to generate an output signal to monitor charging operations, and a comb filter. The comb filter is configured to apply filtering to the output signal to remove noise from the output signal, wherein the filtering is applied based on the charging frequency. The external charging device is configured to process the filtered output signal to detect a circuit state of charging circuitry of the implantable medical device during charging operations, and the external charging device is configured to vary the charging frequency based, in part, on detection of the circuit state of the charging circuitry of the implantable medical device.

In the description herein for embodiments of the present disclosure, numerous specific details are provided, such as examples of circuits, devices, components, and/or methods, etc., to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth with respect to an implantable pulse generator (IPG) configured for generating electrical stimulation for application to a desired area of a body or tissue based on a suitable stimulation therapy application, such as a spinal cord stimulation (SCS) system. However, it should be understood that example wireless power transfer circuitry and methods of operation disclosed herein are not limited thereto, but have broad applicability, including but not limited to different types of implantable devices such as neuromuscular stimulators and sensors, dorsal root ganglion (DRG) stimulators, deep brain stimulator (DBS) devices, cochlear stimulators, retinal implanters, drug delivery systems, muscle stimulators, tissue stimulators, cardiac stimulators, gastric stimulators, and the like, including other bioelectrical sensors and sensing systems, which may be broadly referred to as "biostimulation" applications and/or implantable medical devices (IMDs) for purposes of the present disclosure. Moreover, example circuitry and methods of operation disclosed herein are not limited to use with respect to an IPG or any particular form of IPG or IMD. For example, some embodiments may be implemented with respect to a fully implantable pulse generator, a radio frequency (RF) pulse generator, an external pulse generator, a micro-implantable pulse generator, inter alia.

Figure 7:
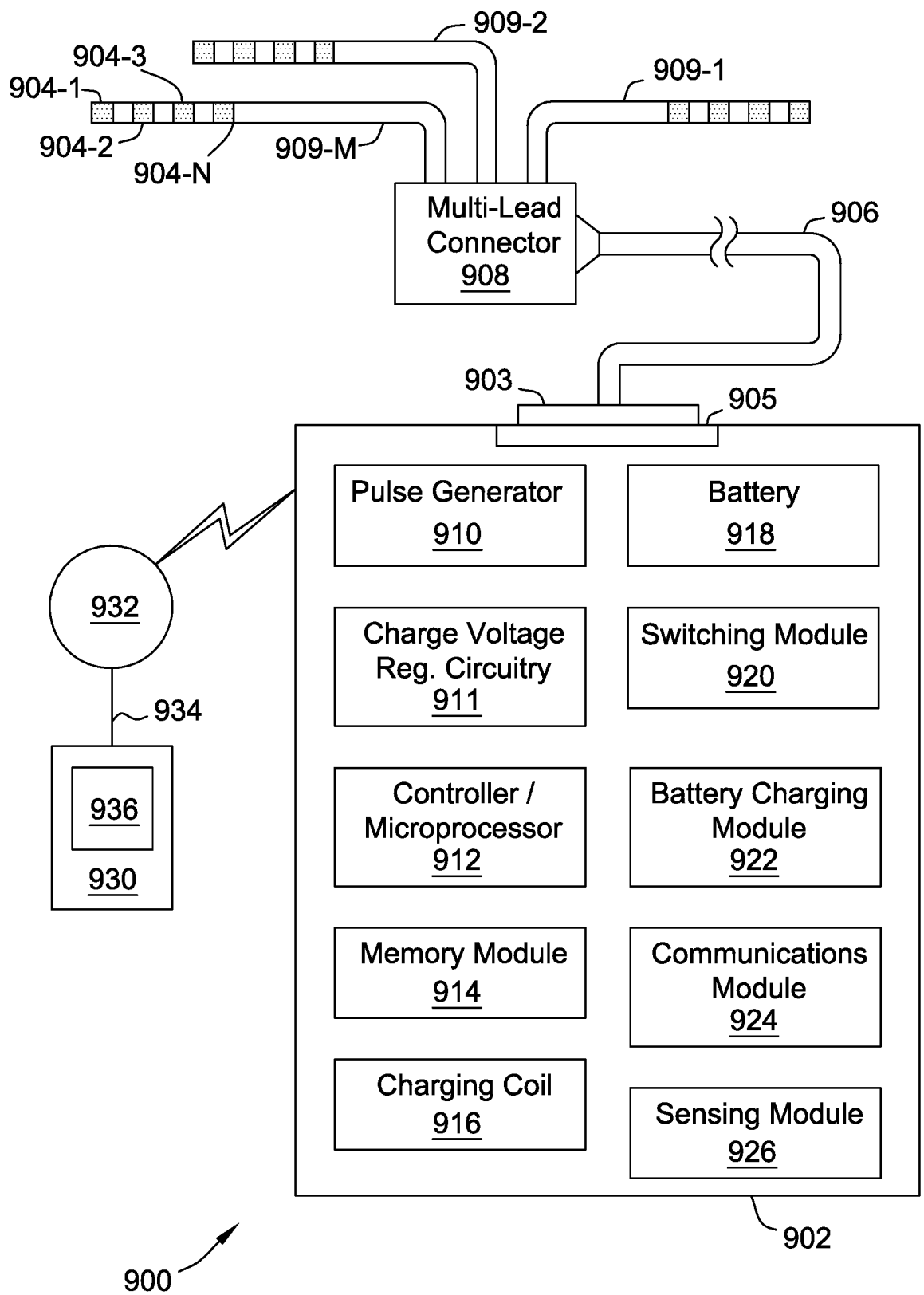
FIG. 7 is a schematic diagram of one embodiment of a biostimulation system.

Referring to FIG. 7 in particular, depicted therein is a biostimulation system 900 wherein one or more embodiments the present disclosure may be practiced in association with an IPG/IMD for achieving optimized wireless power transfer from an external charging system according to the teachings herein. By way of illustration, system 900 may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. System 900 includes IMD 902 having a pulse generator portion that is adapted to include or otherwise interoperate with (re)chargeable battery circuitry for generating suitable stimulation pulses having adjustable target voltages that may be selectively applied for purposes of therapy. IMD 902 may be implemented in one example embodiment as having a metallic housing or can that encloses a controller/processing block or module 912, pulse generating circuitry 910, charging voltage regulation module 911, a charging coil 916, a battery 918, a far-field and/or near field communication block or module 924, battery charging circuitry 922, switching circuitry 920, sensing circuitry 926, one or more memory modules 914, and the like.

Controller/processor module 912 typically includes a microcontroller or other suitable processor for controlling the various other components of IMD 902. Software/firmware code may be stored in memory modules 914, which may be integrated with the controller/processor module 912, and/or other suitable application-specific storage components (not shown in FIG. 9) for execution by the microcontroller or processor 912 and/or other programmable logic blocks to control the various components of IMD 902.

In one embodiment, IMD 902 may be configured to couple to one or more stimulation leads 909-1 to 909-M using an implantable multi-lead connector 908 operative to receive corresponding stimulation leads 909-1 to 909-M at their respective proximal ends for securely engaging and providing electrical connectivity with respect to each stimulation lead's distal end having a plurality of stimulation electrodes. By way of illustration, stimulation lead 909-M is exemplified with stimulation electrodes 904-1 to 904-N, which may be implanted near or adjacent to the patient's target tissue. Stimulation leads 909-1 to 909-M may include percutaneous leads, paddle leads, etc., wherein the electrodes may include ring electrodes, segmented or split electrodes, planar electrodes, and the like, that may be energized by the pulse generating circuitry 910 according to applicable therapy protocols/regimes. In the embodiment shown, a single lead cable 906 may be provided for electrically connecting the multi-lead connector 908 to IPG 902 via a suitable connector interface or socket 903 that may be mated to an interface receptacle or header portion 905 of IMD 902. In general operation, electrical pulses may generated by the pulse generating circuitry 910 under the control of processing block 912, which may be provided to the switching circuitry 920 that is operative to selectively connect to the electrical outputs of the IMD, which are ultimately coupled to one or more electrodes of any combination of leads 904-1 to 904-M at a distal end of the lead system via respective electrical conductive traces An external device 930 may be implemented to charge/recharge the battery 918 of IMD 902, to access memory modules 914, and/or to program or reprogram IMD 902 with respect to the stimulation set parameters including pulsing specifications while implanted within the patient (although a separate recharging device could alternatively be employed). In alternative embodiments, accordingly, separate programmer and charger devices may be employed for charging and/or programming IMD 902 and/or any programmable components thereof. Regardless of whether charging functionalities and communication/programming functionalities are integrated, an example embodiment of the external device 930 may be a processor-based system that possesses wireline and/or wireless communication capabilities, near field magnetic/RF coupling capabilities, etc. Software may be stored within a non-transitory memory of the external device 930, which may be executed by the processor 936 to control the various operations of the external device 930. A connector or "wand" 934 may be electrically coupled to the external device 930 through suitable electrical connectors (not specifically shown), which may be electrically connected to a telemetry/charging component 932 (e.g., inductor coil, RF transceiver, etc.) at the distal end of wand 934 through respective links that allow bi-directional communication with IMD 902. Optionally, in some embodiments, wand 934 may include one or more temperature sensors for use during charging operations.

Turning attention now to FIG. 1, depicted therein is a block diagram of one embodiment of a charging system 100 including an external charger 102 and an IPG device 162 that includes an embodiment of wireless power transfer circuitry according to the teachings herein. For purposes of the present disclosure, example IPG 162 may include any of the IMDs having any number or type of lead systems set forth above. Accordingly, the terms "IMD", "IPG", or related terms of similar import will be somewhat synonymously used in the patent application. In one arrangement, charger 102 may include a controller or processor 104 (e.g., any suitable commercially available microcontroller) for controlling the operations of charger 102 according to instructions stored in non-volatile memory 106. In one arrangement, charger 102 may be powered by a battery 110 having a suitable output voltage range. In some embodiments, battery 110 may comprise a rechargeable Lithium (Li) ion battery although other battery types or chemistries may be used. In some further embodiments, inductive step-up converters may be used in conjunction with a battery to obtain a suitable coil drive voltage. External charger 102 also includes charging and communication circuitry 108, which may be adapted or otherwise configured in some embodiments to electrically couple to a coil 107 operating as a charging energy source. In some embodiments, coil 107 may be disposed in an external wand (not shown in FIG. 1) that may be held, during charging, by a patient or an authorized healthcare professional about the patient's body adjacent to an implant site of IMD 162. Alternatively, the charger's coil 107 (which may be referred to as a primary coil) may be integrated in the same device package with the circuitry of charger 110. Charging and communication circuitry 108 may be configured to drive the primary coil 107 using a suitable RF signal for charging purposes. In some arrangements, charging and communication circuitry 108 may also drive the coil 107 using a suitable modulated RF signal to communicate/receive data to/from IMD 162. In still further embodiments, charger 102 may also be adapted for use as a controller to control the operations of IPG 162 by communicating suitable control parameters using circuitry 108, as noted above.

Example IMD 162, which is another representation of IMD 902 described above, is illustrated herein as including controller 164 (e.g., any suitable commercially available microcontroller) for controlling the pulse generation functionalities and other operations of IMD 162 according to instructions stored in non-volatile memory 166. IMD 162 includes pulse generating circuitry 172 for generating stimulation pulses for delivery to tissue of the patient. It should be appreciated that any suitable existing or later developed pulse generating circuitry may be employed. An example of pulse generating circuitry is described in U.S. Patent Application Publication No. 2006/0259098, entitled "SYSTEMS AND METHODS FOR USE IN PULSE GENERATION," which is incorporated herein by reference. Pulse generating circuitry 172 may include one or multiple pulse sources. Also, pulse generating circuitry 172 may operate according to constant voltage stimulation, constant current stimulation, or any other suitable mode of operation.

The various components of IMD 162 are powered by one or more internal batteries 170 (e.g., Li-ion rechargeable batteries). Battery 170 may be recharged by converting RF power radiated or received from external charger 102. Charging and communication circuitry 168 of IMD 162 is operative to couple to a coil 167 (referred to as a secondary coil) for effectuating near field coupling 150 with the coil 107 of external charger 102. When external charger 102 radiates RF power using its coil 107, the inductive coupling between the coil 107 of charger 102 with the coil 167 of IMD 162 causes an alternating current to be induced in the coil 167 of IMD 162. As will be set forth in detail further below, at least a portion of circuitry 168 may be configured to utilize the induced current in order to provide a charging voltage to battery 170 in a controllable manner. Also, in some embodiments, circuitry 168 may optionally use the same coil 167 to effectuate control communications signaling with charger 102. Further, one embodiment of the present disclosure advantageously uses only two feedthrough connections for connecting a coil-based frontend portion disposed in the header portion of IMD 162 to the rest of the internal circuitry of IMD 162. As skilled artisans will appreciate, the pulse generation circuitry 172 may be coupled to one or more stimulation leads through electrical connections provided in the header portion of the IMD's housing (i.e., feedthroughs), and by minimizing the number of feedthroughs used for connecting electrical conductors for other purposes (e.g., charging/communications), the number of leads that may be deployed in a stimulation therapy system may be advantageously maximized.

Figure 2:
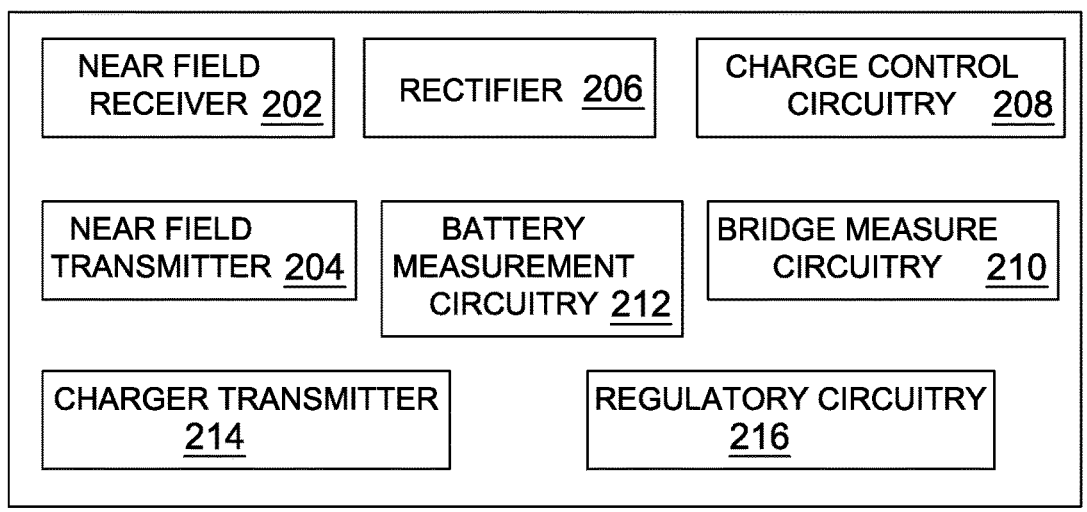
FIG. 2 is a block diagram of one embodiment of charging circuitry that may be used with the charging system shown in FIG. 1.

FIG. 2 depicts a block diagram of charging circuitry 200, which is a further representation of circuitry 168 of FIG. 1, illustrating additional components thereof according to one example embodiment. Circuitry 200 includes coil and bridge rectifier circuitry 206, wherein a coil thereof (e.g., secondary coil 167 shown in FIG. 1) may be used for charging operations as well as communications with an external charger (e.g., charger 102) in some embodiments. In some other embodiments, the secondary coil may be used only for charging, with alterative links being available for communication purposes as previously noted. A near field receiver 202 is coupled to the coil, e.g., through a suitable capacitive arrangement. In one arrangement, receiver 202 may be configured to demodulate data when a carrier at an appropriate frequency is detected, whereupon a data stream may be communicated to controller 164. In similar fashion, near field transmitter 204 may be configured in one arrangement to receive a data stream from controller 164 for generating a modulated RF signal therefor, which may be applied to the secondary coil to communicate data via NFC to charger 102. Signal modulation and demodulation may, alternatively, be implemented in software executing on controller 164. Further, in some example embodiments, near field receiver 202 and transmitter 204 may be configured to not operate (e.g., disabled) when charging operations are taking place. Accordingly, a separate charger transmitter 214 may be employed to provide charging status messages to charger 102 when charging/discharging operations are being effectuated.

In one example arrangement, bridge measurement circuitry 210 may be provided to measure the output voltage of a bridge rectifier for control of charging operations. Regulatory circuitry 216 may be configured to control charging operations in response to one or more feedback/measurement signals (e.g., from bridge measurement circuitry 210). In one embodiment, when the output voltage is relatively low, regulatory circuitry 216 may be configured to allow circuitry 200 of the IMD to absorb RF power. Likewise, when the output voltage is relatively high, the coil may be clamped (e.g., shorted to ground) to prevent absorption of RF power in an example arrangement.

Charge control circuitry 208 may be provided to control the charging of battery 170. In one embodiment, charge control circuitry 208 may be configured to use the measurement functionality of battery measurement circuitry 212 to detect the state of battery 170. By way of illustration, battery measurement circuitry 208 may measure the battery voltage, charging current, battery discharge current, and/or the like. In some example embodiments, charge control circuitry 208 may prevent battery charging when an end-of-life (EOL) state has been reached for battery 154, which may be determined responsive to measurements provided by battery measurement circuitry 212. In further embodiments, charge control circuitry 208 may be configured to use a number of measurements to conduct fast charging operations as disclosed in greater detail in U.S. Patent Application Publication No. 2006/0259098, entitled "SYSTEMS AND METHODS FOR USE IN PULSE GENERATION," incorporated by reference herein. In still further embodiments, charge control circuitry 208 may also be configured to monitor one or more output signals from bridge measurement circuitry 210 to further regulate the output voltage from bridge rectifier circuitry 206.

Figure 3:
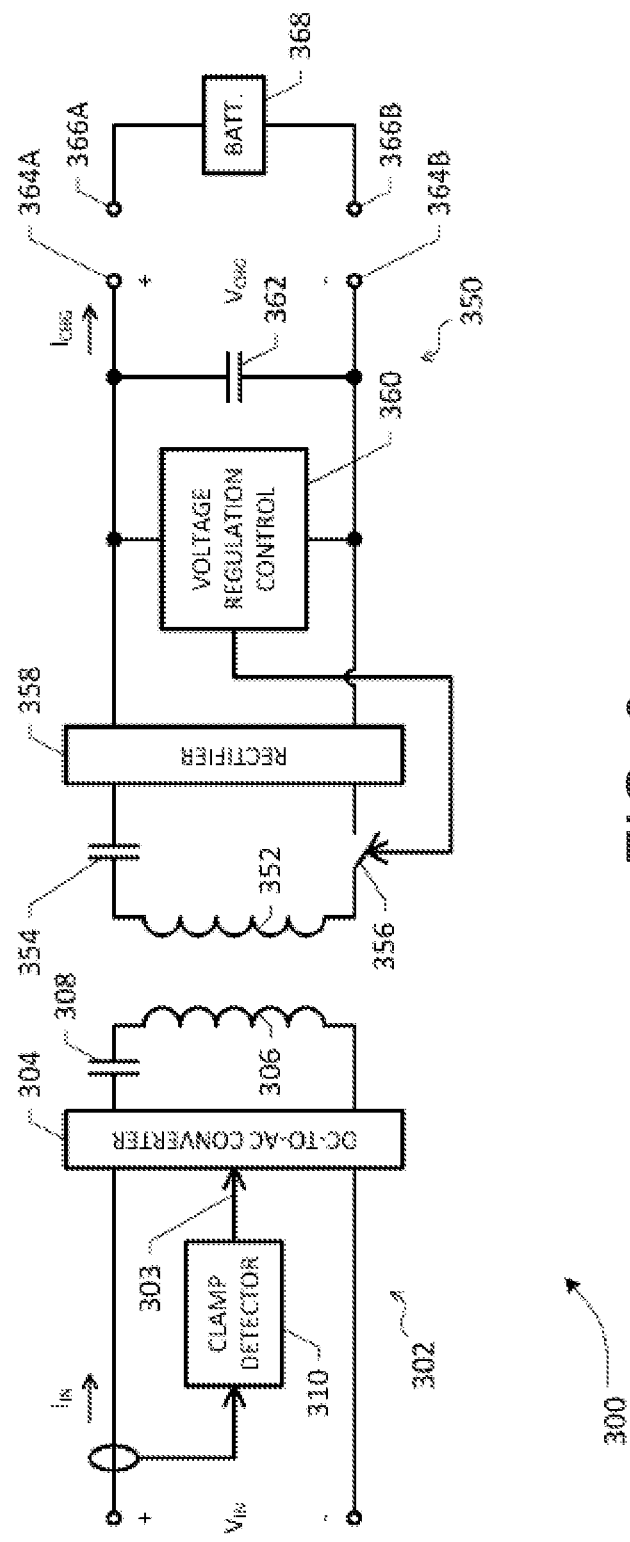
FIG. 3 is a high level circuit block diagram of one embodiment of a wireless charging system.

FIG. 3 is a high level circuit block diagram of a wireless charging system 300 for purposes of an example embodiment of the present disclosure. Broadly, a power sender block 302 is operative as an external charger that supplies RF energy to a power receiver block 350 (e.g., an IMD) through respective series resonant coils that operate as a loosely coupled transformer (i.e., via magnetic coupling). A DC voltage input (V1N) having a suitably configurable voltage range is provided to the power sender block 302, which includes a DC-to-AC converter 304 coupled to a sender-side tuning circuit including a primary coil 306 and a capacitor 308 connected in series. A clamp detector/monitor 310 may be included in the power sender block 302 for sensing the state of input current (11N). In one example embodiment, clamp detector/monitor 310 may be configured to generate a control signal 303 to DC-to-AC converter 304 in response to the input current status. It should be appreciated that DC-to-AC converter 304 is operative as a coil driver in order to supply adequate RF power to the power receiver block 350. When power receiver block 350 is not accepting power during a charging cycle (e.g., due to internal voltage/charging regulation and/or other internal ambient and status control signals), current flow through the sender-side tuning circuit is negligible (i.e., turned off), a condition which may be sensed as a status change in the input current by the clamp detector/monitor circuitry 310 to generate control signal 303 operative to deactivate the power sender circuitry during the off state, thereby saving power. To effectuate near field inductive RF power transfer, the power receiver block 350 is provided with a receiver-side tuning circuit including at least a secondary coil 352 coupled to at least a capacitor 354 in series (e.g., similar to the sender-side tuning circuit arrangement). An induced AC signal from the receiver-side tuning circuit is rectified by a rectifier 358, whose output may be optionally and/or suitably conditioned to apply power to a load, i.e., a battery 368 having terminals 366A, 3668. In an example arrangement, battery 368 may be disposed between output nodes 364A, 3648 of conditioning circuitry having an output capacitor arrangement (Cout) 362 for providing a suitable DC output voltage (Vchg or Vout). In one example embodiment, voltage regulation control circuitry 360 may be coupled between the rectifier/conditioning portion 358 and battery load 368, which may be configured to generate one or more control signals for controlling a series switch arrangement 356 connected to the receiver-side tuning circuit arrangement, as will be set forth in further detail below.

It should be appreciated that the relationships between the sender-side coil voltage and current and the receiver-side coil voltage and current may be determined in an example implementation by the series tuning of the respective coils. For instance, such relationships may depend upon the operating frequency, tuning accuracy, coil separation, coil geometries, and the like. Accordingly, power transfer in an example arrangement involving wireless charging system 300 may in general depend on coupling between coils 306, 352, which in turn may depend on the distance between coils 306, 352, alignment, coil dimensions, coil materials, respective number of turns, magnetic shielding, impedance matching, applicable power band and associated resonant frequency, duty cycle, etc. Skilled artisans will recognize that at least some of these parameters may be selected in the design of an embodiment in order to comply with known or heretofore unknown wireless power transfer standards and specifications (e.g., Wireless Power Consortium WPC 1.1 Standard). Further, the voltage regulation control circuitry 360 may be appropriately configured in an example embodiment such that the time spent in the ON and OFF states may be suitably designed depending on the IMD application.

In an example embodiment, accordingly, the time spent in the ON and OFF states may be determined based on an applicable voltage hysteresis band (VHIGH–VLOW), the rectifier output current, and the load current. In one example embodiment, an upper output threshold voltage VHIGH that begins clamping may be selected to be at 4.5V and a lower threshold voltage VLOW that ends clamping may be selected to be at 4.37 V, resulting in a nominal voltage hysteresis voltage of 0.13 V. In an example embodiment, the power sender block 302 may be configured to continually adjust its RF output power to maintain at least substantially constant power transfer to the power receiver block 350 across a range of distances. Further, certain additional design criteria may be implemented in order to achieve maximum power transfer efficiency in an implementation. For example, one requirement may be that the charger, i.e., power sender block 302, should deliver a select battery charging current suitable for a use case or application scenario. In an example use case, such a requirement may comprise a charging current of 50 mA. Another design requirement may be that the charger should deactivate during the OFF states to conserve power.

Accordingly, in one arrangement, the clamp detector/monitor circuit 310 of the power sender block 302 may be configured to sense the time periods between clamping events of the power receiver block 350 in order to modulate the output power, as previously noted. Related details with respect to utilizing a clamp detection signal in a charging system may be found in U.S. Pat. No. 8,731,682, entitled "EXTERNAL CHARGING DEVICE FOR CHARGING AN IMPLANTABLE MEDICAL DEVICE AND METHODS OF REGULATING DUTY CYCLE OF AN EXTERNAL CHARGING DEVICE," incorporated herein by reference in its entirety.

An example implementation of the wireless charging system 300 set forth above may be advantageously configured such that it involves only two feedthrough connections for connecting the receiver-side tuning circuit including coil 352 and capacitor 354 to the rest of the IPG internal circuitry. Moreover, the series switch arrangement 356 may be configured such that the receiver-side tuning circuit may be detuned or otherwise disabled during the OFF condition, thereby advantageously eliminating a high voltage condition that can develop during the time when the power receiver block 350 is in the clamped state because the receiver-side tuning circuit may be in resonance. As one skilled in the art will appreciate, the voltage in the secondary coil 352 may reach relatively high levels in the clamped state in some implementations (e.g., as high as 300V), which may be undesirable.

To achieve effective charging between an external charging device (such as external charger 102 (shown in FIG. 1)) and an IMD (such as IMD 162 (also shown in FIG. 1), in some embodiments, the external charging device changes its magnetic frequency to accommodate for distance and misalignment (e.g., due to a relative orientation) between the external charging device and the IMD. However, these frequency changes may introduce noise into the signal transmitted by the external charging device, increasing the noise floor and reducing a signal to noise ratio. Low signal to noise ratios may reduce charging range, and inhibit ability to detect information embedded in the signal (e.g., battery status, etc.). Accordingly, the embodiments described herein facilitate reducing and improving the signal to noise ratio of signals transmitted by an external charging device.

Specifically, the systems and methods described herein enable filtering out noise that has the signature of noise produced by charging circuitry in an external charging device (such as external charger 102 (shown in FIG. 1)). The embodiments described herein may be implemented entirely digitally, and advantageously remove noise in a tunable system (such as a system for charging a rechargeable IPG). As described herein, a comb filter stage is added in a data acquisition path of the external charging device. This provides a tunable filter solution for the frequency that is being generated by the coil on the external charging device (e.g., coil 107). In one embodiment, the comb filter is a forward comb filter. Alternatively, the comb filter may be any suitable type of comb filter. Although at least some of the embodiments disclosed herein involve a digital implementation, those of skill in the art will appreciated that hardware implementations of the filtering techniques described herein may also be used.

Figure 4:
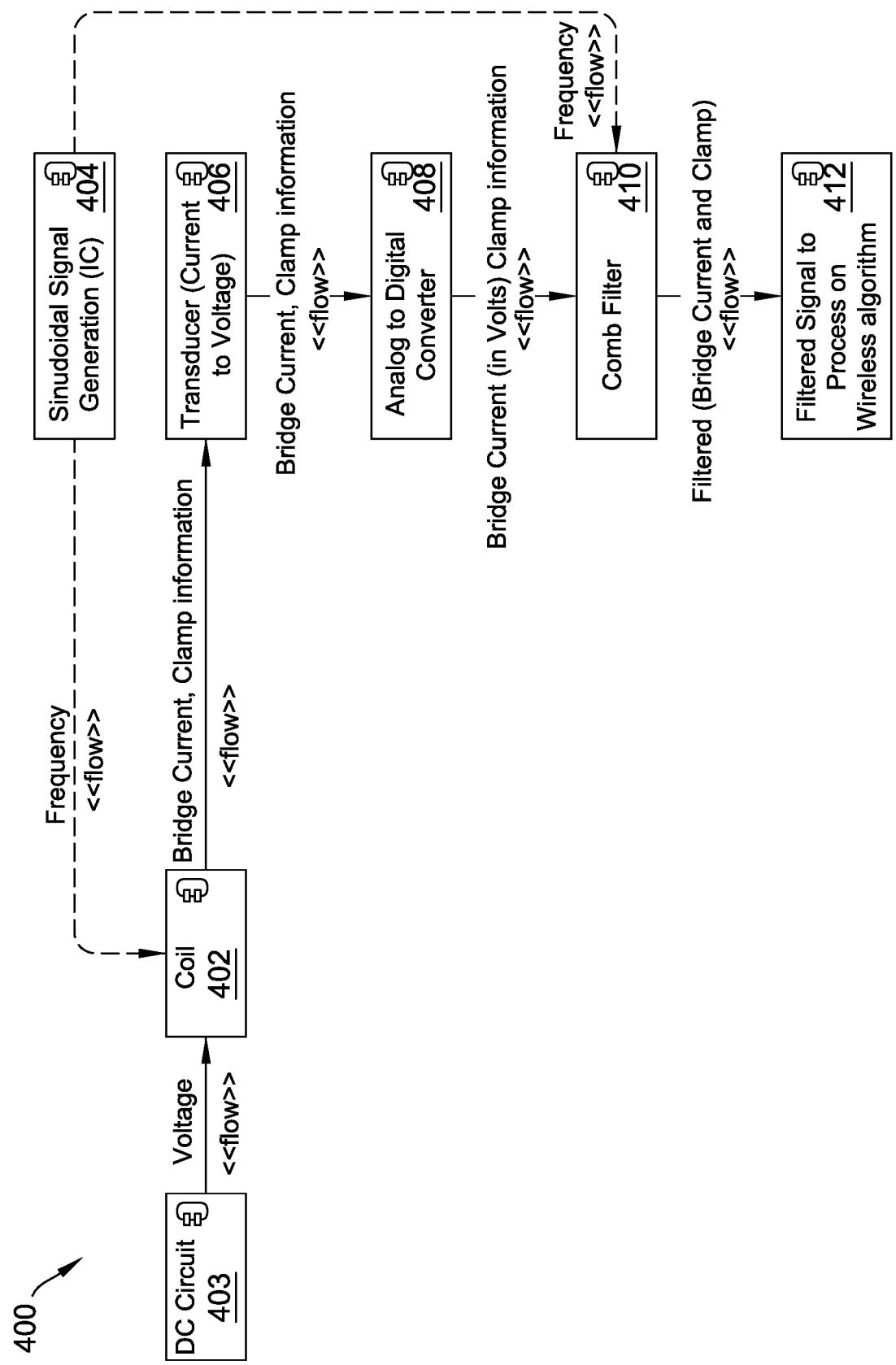
FIG. 4 is a block diagram of one embodiment of an architecture that may be used with the charging system shown in FIG. 1.

FIG. 4 is a diagram of an architecture 400 that may be used to reduce noise in a signal produced by an external charging device. Architecture 400 is implemented within the external charging device (such as external charger 102 (shown in FIG. 1)).

As shown in FIG. 4, a coil 402 generates the desired magnetic field at a frequency controlled by sinusoidal signal generating integrated circuitry (IC) 404. Coil 402 is driven using DC circuitry 403 in this embodiment. As this occurs, a transducer 406 coupled to coil 402 converts a bridge current through coil 402 into a voltage. This signal (the bridge current converted into a corresponding voltage) is digitized by an analog to digital converter 408. Transducer 406 and analog to digital converter 408 are one example of monitoring circuitry that may be included within architecture 400. A comb filter 410 (e.g., a forward comb filter) is then applied to the digital output of analog to digital converter 408, outputting a filtered signal 412 for transmission to the implantable device.

Comb filter 410 receives the frequency from sinusoidal signal generating IC 404, and filters the digital output based on the frequency output by the sinusoidal signal generating IC 410 (i.e., the same frequency that coil 402 operates at). Accordingly, comb filter 410 is tuned to the frequency that coil 402 operates at.

Those of skill in the art will appreciate that architecture 400 is merely an example, and that other implementations of using a comb filter to reduce noise in a signal generated by a charging device fall within the spirit and scope of the disclosure.

Figure 5:
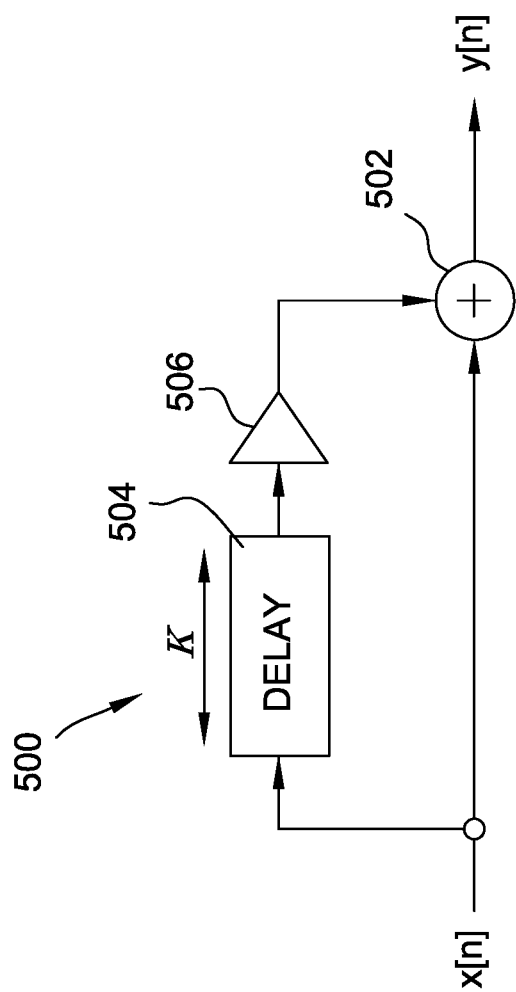
FIG. 5 is a circuit diagram of one embodiment of a comb filter that may be used with the architecture shown in FIG. 4.

FIG. 5 is a circuit diagram of a comb filter 500 that may be used to implement comb filter in architecture 400. Comb filter 500 operates by adding a delayed version of a signal to itself, causing constructive and destructive interference.

In comb filter 500, an input signal (x[n]) is summed (using a summing circuit 502) with a delayed version of the input signal (delayed using a delay circuit 504) that may be scaled by a scaling factor using a scaling circuit 506). The resulting sum is the output signal (y[n]) of comb filter 500. In the context of architecture 400, the input signal would be the digital output of analog to digital converter 408.

Figure 6:
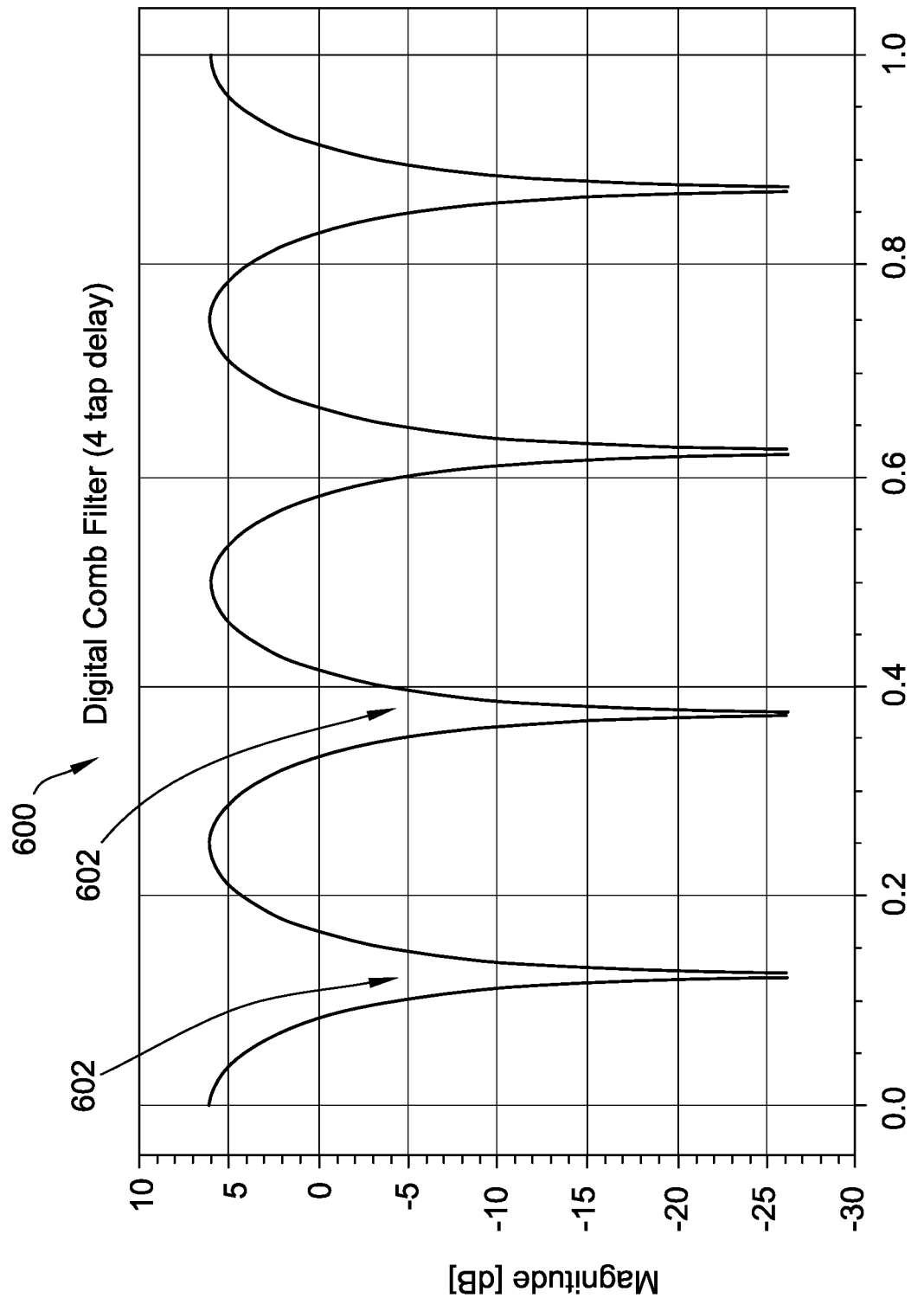
FIG. 6 is a graph illustrating an example frequency response of a comb filter.

FIG. 6 is a graph 600 illustrating an example frequency response of a comb filter (e.g., comb filter 500). As shown in FIG. 6, by summing a signal with a delayed version of itself, a comb filter generates a frequency response with a series of notches 602.

In some embodiments, external charger 102 is adapted to prevent undesirable conditions in IMD 162 by processing the filtered signal from comb filter 410. For example, during charging operations, external charger 102 may attempt to reduce the power transfer during inductive charging by modifying the charging frequency when the filtered signal from comb filter 410 indicates that excessive power is being transferred to IMD 162. If frequency modification does not reduce the power transfer level to an appropriate level, external charger 102 may temporarily cease charging operations (i.e., cease driving current through charging coil 306 (Shown in FIG. 3)).

In such circumstances, external charger 102 may be positioned too close to IMD 162 and the coupling to IMD 162 is too high (e.g., the external charger 102 may be positioned in a "hot spot"). Positioning of external charger 102 in a "hot spot" may cause excessive voltages in IMD 162 and/or excessive heating of IMD 162. Repositioning of external charger 102 may improve the coupling between the external charger 102 and IMD 162. Accordingly, external charger 102 may be adapted to indicate to the patient that the patient should reposition external charger 102 so that the charging may resume in a safe or proper manner. External charger 102 may provide audible, visual, tactile, or other suitable feedback to the user to reposition external charger 102. Also, a separate device (e.g., a "patient controller" device) may display a repositioning message upon wireless communication with external charger 102 in such circumstances.

In the embodiments described herein, to remove noise from the signal generated by the external charging device, operation of the comb filter is adjusted based on the frequency at which the coil operates. This provides a tunable comb filter algorithm.

As shown in FIG. 4, comb filter 410 is applied to coil bridge current data (after conversion to a corresponding voltage and digitization). To implement the noise filtering described herein, the embodiments described herein may include a buffer (i.e., a memory device) including the coil bridge current data, as well as a buffer including frequency values at which coil 402 is operated (e.g., both current and historical frequency values).

The embodiments described herein provide systems and methods for wirelessly charging an implantable medical device. An external charging device includes a coil, signal generating circuitry to drive current through the coil at a charging frequency to induce current in a second coil in the implantable medical device, monitoring circuitry to generate an output signal to monitor charging operations, and a comb filter. The comb filter is configured to apply filtering to the output signal to remove noise from the output signal, wherein the filtering is applied based on the charging frequency. The external charging device is configured to process the filtered output signal to detect a circuit state of charging circuitry of the implantable medical device during charging operations, and the external charging device is configured to vary the charging frequency based, in part, on detection of the circuit state of the charging circuitry of the implantable medical device.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An external charging device for wirelessly charging an implantable medical device, the external charging device comprising:
    a coil;
    signal generating circuitry coupled to the coil to drive current through the coil at a charging frequency to induce current in a second coil in the implantable medical device;
    monitoring circuitry coupled to the coil to generate an output signal to monitor charging operations; and
    a comb filter coupled to the monitoring circuitry, the comb filter configured to apply filtering to the output signal generated by the monitoring circuitry to remove noise from the output signal, wherein the filtering is applied based on the charging frequency;
    wherein the external charging device is configured to process the filtered output signal to detect a circuit state of charging circuitry of the implantable medical device during charging operations; and
    wherein the external charging device is configured to vary the charging frequency based, in part, on detection of the circuit state of the charging circuitry of the implantable medical device.

2. The external charging device of claim 1, wherein the external charging device is configured to change the charging frequency to control a level of power transfer to the implantable medical device.

3. The external charging device of claim 1, wherein the external charging device is configured to estimate a distance between the external charging device and the implantable medical device based on the charging frequency.

4. The external charging device of claim 1, wherein the external charging device is configured to modify the charging frequency based on a distance between the external charging device and the implantable medical device.

5. The external charging device of claim 1, wherein the external charging device is configured to modify the charging frequency based on an orientation of the external charging device relative to the implantable medical device.

6. The external charging device of claim 1, wherein the external charging device is configured to cease charging operations when processing of the filtered output signal indicates potential excessive heating of the implantable medical device.

7. The external charging device of claim 1, wherein the external charging device is configured to provide a signal to a user of the external charging device to reposition the external charging device to reduce potential excessive heating of the implantable medical device.

8. The external charging device of claim 1, wherein the monitoring circuitry comprises:
   a transducer coupled to the coil, the transducer configured to convert a bridge current generated by the coil into a corresponding voltage; and
   an analog to digital converter coupled between the transducer and the comb filter, the analog to digital converter configured to digitize the corresponding voltage, wherein the comb filter is configured to apply filtering to the digitized voltage.

9. The external charging device of claim 1, wherein the comb filter is a forward comb filter.

10. A wireless charging system comprising:
   an implantable medical device comprising charging circuitry; and
   an external charging device configured to wirelessly charge the implantable medical device, the external charging device comprising:
      a coil;
      signal generating circuitry coupled to the coil to drive current through the coil at a charging frequency to induce current in a second coil in the implantable medical device;
      monitoring circuitry coupled to the coil to generate an output signal to monitor charging operations; and
      a comb filter coupled to the monitoring circuitry, the comb filter configured to apply filtering to the output signal generated by the monitoring circuitry to remove noise from the output signal, wherein the filtering is applied based on the charging frequency;
   wherein the external charging device is configured to process the filtered output signal to detect a circuit state of the charging circuitry of the implantable medical device during charging operations; and
   wherein the external charging device is configured to vary the charging frequency based, in part, on detection of the circuit state of the charging circuitry of the implantable medical device.

11. The wireless charging system of claim 10, wherein the external charging device is configured to change the charging frequency to control a level of power transfer to the implantable medical device.

12. The wireless charging system of claim 10, wherein the external charging device is configured to estimate a distance between the external charging device and the implantable medical device based on the charging frequency.

13. The wireless charging system of claim 10, wherein the external charging device is configured to modify the charging frequency based on a distance between the external charging device and the implantable medical device.

14. The wireless charging system of claim 10, wherein the external charging device is configured to modify the charging frequency based on an orientation of the external charging device relative to the implantable medical device.

15. A method for operating an external charging device in a wireless charging system, the method comprising:
   driving, using signal generating circuitry of the external charging device, current through a coil at a charging frequency to induce current in a second coil in an implantable medical device;
   generating, at monitoring circuitry of the external charging device, an output signal to monitor charging operations;
   applying, using a comb filter of the external charging device, filtering to the output signal generated by the monitoring circuitry to remove noise from the output signal, the filtering applied based on the charging frequency;
   processing the filtered output signal to detect a circuit state of charging circuitry of the implantable medical device during charging operations; and
   varying the charging frequency based, in part, on detection of the circuit state of the charging circuitry of the implantable medical device.

16. The method of claim 15, further comprising changing the charging frequency to control a level of power transfer to the implantable medical device.

17. The method of claim 15, further comprising estimating a distance between the external charging device and the implantable medical device based on the charging frequency.

18. The method of claim 15, further comprising modifying the charging frequency based on a distance between the external charging device and the implantable medical device.

19. The method of claim 15, further comprising modifying the charging frequency based on an orientation of the external charging device relative to the implantable medical device.

20. The method of claim 15, further comprising ceasing charging operations when processing of the filtered output signal indicates potential excessive heating of the implantable medical device.

* * * * *